United States Patent [19]

Barker

[11] 4,365,636
[45] Dec. 28, 1982

[54] METHOD OF MONITORING PATIENT RESPIRATION AND PREDICTING APNEA THEREFROM

[75] Inventor: Kent R. Barker, Cottage Grove, Minn.

[73] Assignee: Medicon, Inc., Minneapolis, Minn.

[21] Appl. No.: 275,343

[22] Filed: Jun. 19, 1981

[51] Int. Cl.³ .............................................. A61B 5/08
[52] U.S. Cl. .................................................. 128/716
[58] Field of Search ....................... 128/716, 720, 724; 364/417

[56] References Cited

U.S. PATENT DOCUMENTS 4,279,257  7/1981  Hochstein ........................... 128/722

Primary Examiner—Kyle L. Howell
Assistant Examiner—John C. Hanley

[57] ABSTRACT

A method for detecting apnea by sampling a voltage waveform representative of respiration at regular intervals and calculating the instantaneous voltage differences at alternate sample points, and comparing the magnitude of each difference voltage so calculated against a "threshold" value determined to be the minimum value consistent with normal respiration activity.

23 Claims, 7 Drawing Figures

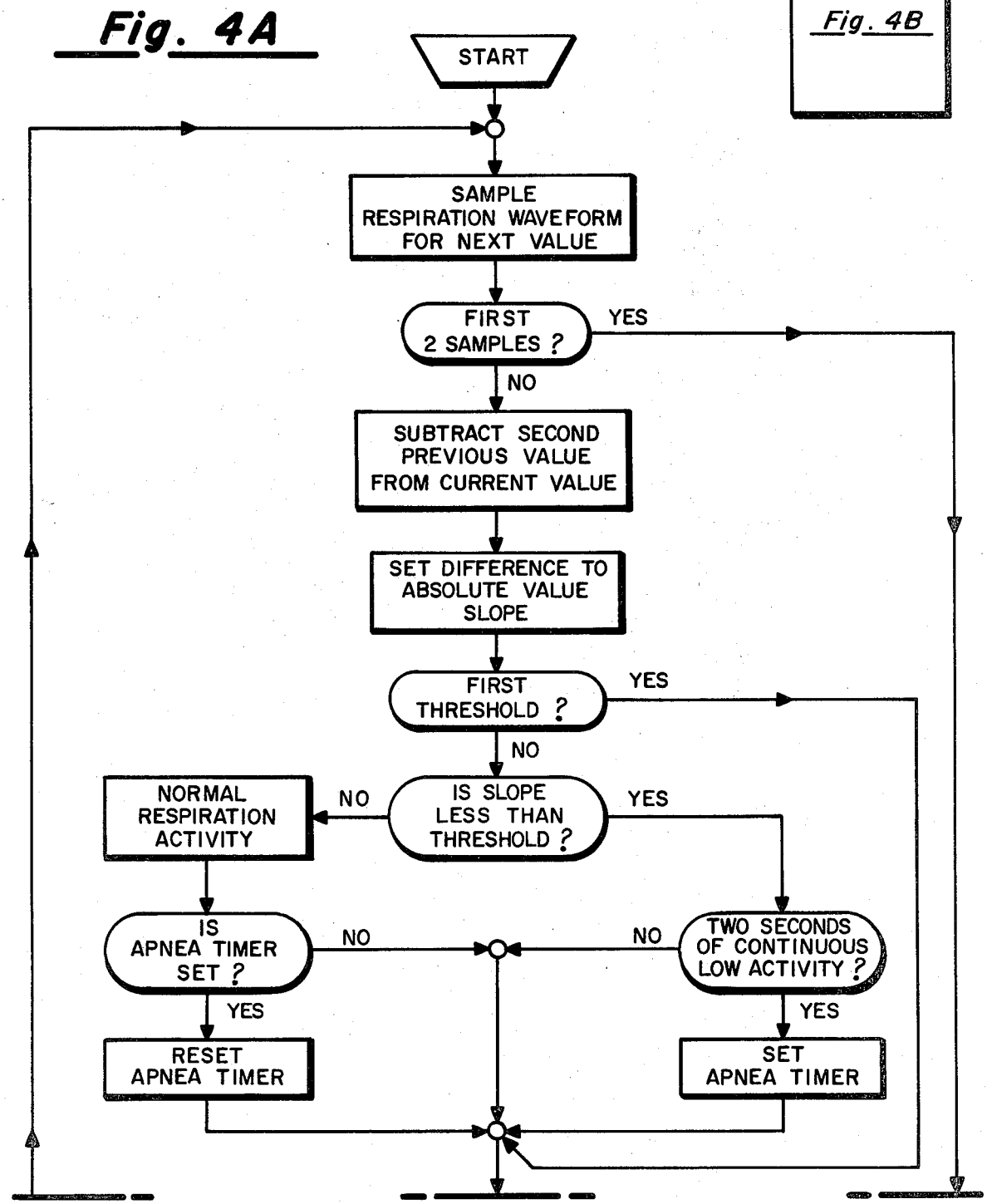

METHOD OF MONITORING PATIENT RESPIRATION AND PREDICTING APNEA THEREFROM

BACKGROUND OF THE INVENTION

This invention relates to a method for monitoring patient respiration; more particularly, the invention relates to a method for monitoring patient respiration by evaluation of an electrical signal generated by an electrode coupled to the patient during respiration. The invention is primarily intended for respiration monitoring and analysis in furtherance of the detection and prediction of apnea.

The medical term "apnea" means cessation of respiration or breathing. The apneic condition has become associated in recent years with the "sudden infant death syndrome", wherein a disturbing pattern of early deaths of apparently healthy infants were noted. Studies and research programs have been conducted by agencies of the federal government and others in an attempt to identify the cause of sudden infant death syndrome, and such studies have revealed that infants who are subject to this syndrome are apparently not the healthy infants before death that they were once believed to be. These infants appear to have subtle and anatomic and physiological defects of a neurologic, cardiorespiratory and/or metabolic nature. There has developed evidence that the syndrome is not caused by a single mechanism working at one moment in time, but rather by a number of developmental, environmental, and pathologic factors which become involved in complex interactions and circumstances to set up a sequence of events that produces the sudden, unexpected and unexplained infant death. Much of this research has revolved around the hypothesis that apnea during sleep is related to the syndrome. It has also been postulated that apneic episodes during sleep which do not necessarily lead to sudden infant death may lead to aberrations in central nervous system development. There is evidence that with infants having numerous apneic episodes during sleep, the resulting inadequate oxygen supply to the brain may lead to retardation of brain development, which in turn may lead to further loss of respiratory control and further apneic problems.

Apnea may be caused by a number of other factors not necessarily related to conditions of infants, some of which are spinal cord injury, muscular dystrophy, lung diseases, drug intoxication, and certain other risk factors which have become apparent in aid of the identification of those who might be candidates or may suffer higher than normal risk for incurring apneic events. In adults, a history of heavy snoring denotes an individual at risk to apnea, especially in combination with other such factors as obesity, underlying heart desease and/or high blood pressure.

Whereas apneic conditions may be monitored in hospital and laboratory environments by means of suitably connected electrodes to a patient's body, and monitoring of a cathode ray tube (CRT) display which exhibits a wave form related to patient respiration, such monitoring is impractical or impossible in less controlled environments. There is therefore a need for techniques and devices which will enable appropriate monitoring of adults or infants and which will detect apneic conditions in time to set off an alarm in order that the condition may be corrected. For sleeping patients, it is frequently only necessary to wake the patient by means of an audible alarm or other alarm indication in order that the patient may become conscious and resume normal breathing. It is therefore important that techniques and devices be developed for utilization in conjunction with sleeping individuals, in order that apneic episodes may be detected and corrected before physiological damage or harm occurs. In all events, the detection of apnea requires a monitoring of respiration and/or heart rates. Such monitoring is accomplished by means of the attachment or coupling of suitable electrodes or other transducer devices to the patient, so that signals developed by such devices may be transmitted to circuitry for detection and analysis. Monitoring transducers are well-known in the art, as for example the respiration monitoring apparatus described in U.S. Pat. No. 3,760,794, issued Sept. 25, 1973. This device is a capacitor transducer constructed from alternate layers of conductive and nonconductive materials which are placed beneath a patient in a mattress or other resilient support, and which detects motion caused by respiration. In other devices, electrodes are attached to the body to detect changes in body impedance or resistance as respiration occurs. In still other devices, pressure sensing transducers are used in the chest and/or stomach area of the body to detect pressure changes which occur as body movement occurs during respiration. All of these transducers, as well as other similar devices, monitor a physical parameter which is correlated with respiration, convert the parameter monitored into an equivalent electrical signal, and feed this signal into appropriate circuitry whose ultimate function is to note the occurance of a respiration cycle and to perform such other functions as are deemed necessary.

SUMMARY OF THE INVENTION

It is a general object of this invention to provide a method and process for the analysis of electrical signals representative of respiration, for the purpose of detecting and predicting apnea. It is a further object of the present invention to provide a method for analyzing respiration wave forms, for setting an alarm condition upon the detection of an apneic episode.

It is another object of the invention to provide a method for analyzing respiration waveforms and for detecting apnea, wherein the method and detection parameters self adjust for changing conditions of respiration.

The invention includes the step of sampling voltages representative of respiration at a predetermined and constant rate, and collecting a plurality of voltage points therefrom; the step of calculating waveform slope by utilizing collected voltage points separated by at least one sample interval; the step of comparing the slope so calculated against a predetermined threshold value which itself has been determined from monitoring of the respiration waveform; and the step of setting an alarm condition whenever the compared slopes remain less than the threshold value for a predetermined length of time.

An important and preliminary part of the invention is the process for developing a threshold value from observation and analysis of respiration waveforms. This portion of the invention involves the steps of calculating wave form slope values for a predetermined length of time, which time is longer than the time necessary for at least one respiration cycle; selecting the maximum slope value obtained over the predetermined time; repeating these steps for a predetermined longer time, which longer time approaches a steady state respiration condition; averaging all of the collected slope values to calculate a "bench mark" slope value; determining a threshold value which is a predetermined fraction of the "bench mark" slope value, the fraction being large enough to detect respiration activity which is representative of an apneic condition and small enough to ignore respiration activity considered representative of a non-apneic condition.

BRIEF DESCRIPTION OF THE DRAWINGS

FIGS. 4A and 4B shows a flow chart of the method; and

DESCRIPTION OF THE PREFERRED EMBODIMENT

Figure 1:
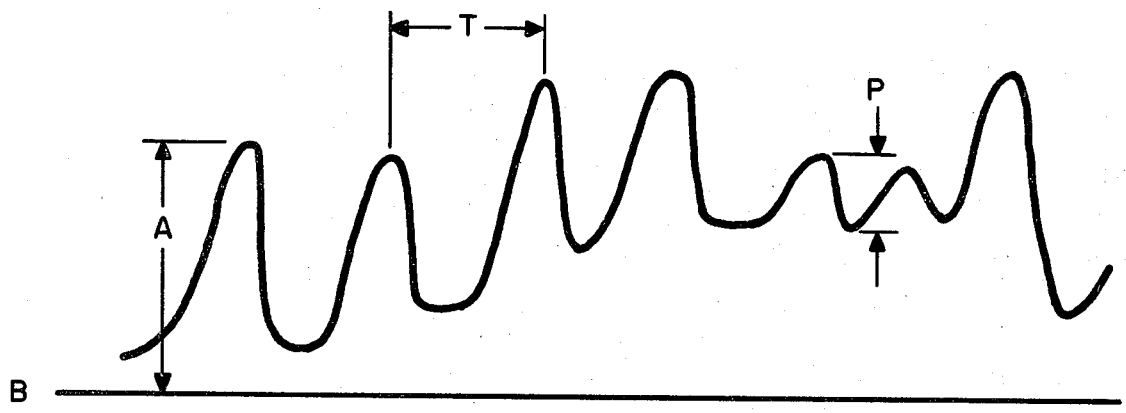
FIG. 1 shows a typical respiration waveform.

Referring first to FIG. 1, there is shown a waveform which is representative of respiration activity as may typically be found in monitoring equipment known in the art. This waveform may be produced by electrical sensors attached directly to the body, or by pressure transducers coupled to the body in one or more of a number of ways. The characteristics of this wave form make it exceedingly difficult to analyze with automatic and unattended electronic or other equipment, whereas a trained technician can readily understand and analyze the waveform while observing it on a cathode ray (CRT) display device. This form of analysis has been widely used in the past, but unfortunately requires the technician to constantly monitor a CRT device in order to detect an apneic condition when one occurs. Some of the waveform parameters which heretofore have defied proper automatic analysis are as follows:

1. The respiration waveform amplitude A, when measured from any arbitrary baseline B, may fluctuate widely and unpredictably during both "normal" respiratory activity and "abnormal" respiration activity;
2. The waveform peak to peak amplitude P may fluctuate widely over all forms of respiration activity;
3. The waveform period T may range over very wide time values from one patient to another, and with respect to a single patient from one time to another; and
4. The waveform shape itself is nonsinusoidal, and therefore requires empirical simplification in order to relate it to normal sinusoidal mathematical treatment, but such empirical simplification must reasonably approximate actual respiration activity so as to provide valid detection without false alarms.

Any method of automatic analysis of the complex waveform of FIG. 1 must therefore take into account all of the variable parameters summarized above, and must also be capable of adapting to real time changes in these parameters such as typically occur during sleep and nonsleep patient activity. For example, a patient while sleeping may undergo periods of deep breathing, followed by subsequent periods of very shallow breathing at higher respiration rates, all of which may be intermittently interrupted by deep sighs or other respiration activity.

It has been empirically determined that respiration rates vary from a high of about two respirations per second to a low of about one respiration per six seconds, and that practically all patients will have respiration rates falling within these bounds. Since the present method contemplates a digital measuring technique, wherein instantaneous waveform magnitudes are sampled at discreet and regular time intervals, the minimum number of such samples necessary for obtaining valid information is therefore governed by the fastest respiration rate. A sampling rate of eight samples per second has been empirically determined to be adequate for obtaining sufficient data points on even the fastest respiration waveform for useful results. Of course, the sample rate could be set higher than eight samples per second to obtain correspondingly more data points, and requiring additional processing of the data so obtained, but it has been determined that eight samples per second gives a reasonable result with a minimum number of data points even at the fastest respiration rates.

It has been empirically determined that a respiration waveform differs in several important characteristics from a pure sinusoidal waveform. Respiration waveforms contain high frequency components which tend to generate a steeper, higher rate amplitude waveform than the comparable pure sinusoidal waveform. For example, it has been determined that the ratio of the maximum waveform slope to the peak waveform amplitude is approximately 1.4 times greater than the same values for a pure sinusoid. Thus, if one is to use this ratio as the base measurement for determining whether the apneic condition exists, and for selecting a threshold value below which an alarm condition should be set, one must select a different threshold level for a respiration waveform than would be selected for a pure sinusoidal waveform. It has been determined that a threshold value of one-half the pure sinusoidal threshold value is required for adequate operation of the method.

The threshold value must be selected low enough such that a wide range of normal respiration waveforms are detected as respiration and not apnea. On the other hand, the threshold must be high enough to prevent false respiration indications during apnea. Since the slowest respiration waveform empirically measured is ten respirations per minute, this is the waveform which forms the basis for selecting the threshold value. This waveform can be represented by a sinusoid having a period of six seconds, and for this waveform it can be shown that selection of a threshold equal to one-half of the peak sinusoidal value will result in values below threshold occurring for no longer than one second. Translating these results to the nonsinusoidal respiration waveform, it has been found that the threshold must be reduced by fifty percent in order for the same relationship to hold; namely, a respiration waveform of six seconds in duration will exhibit no more than one second of time below the threshold value if the threshold value is selected to be 0.25 times the peak value.

Figure 2:
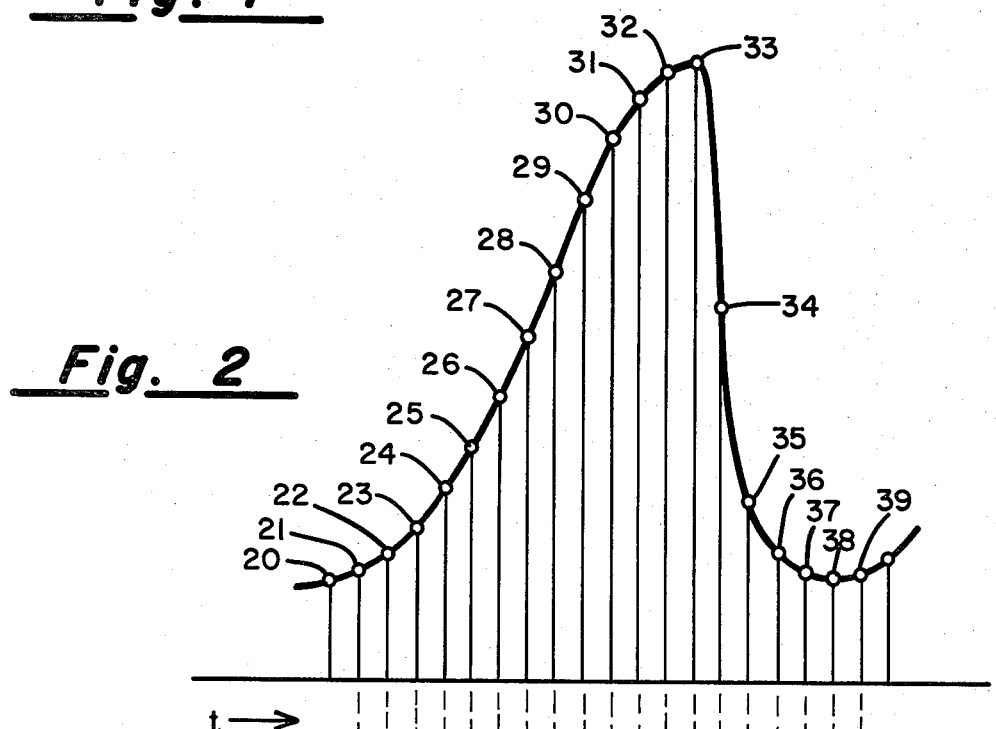
FIG. 2 shows a respiration waveform with periodic voltage sampling.
Figure 3:
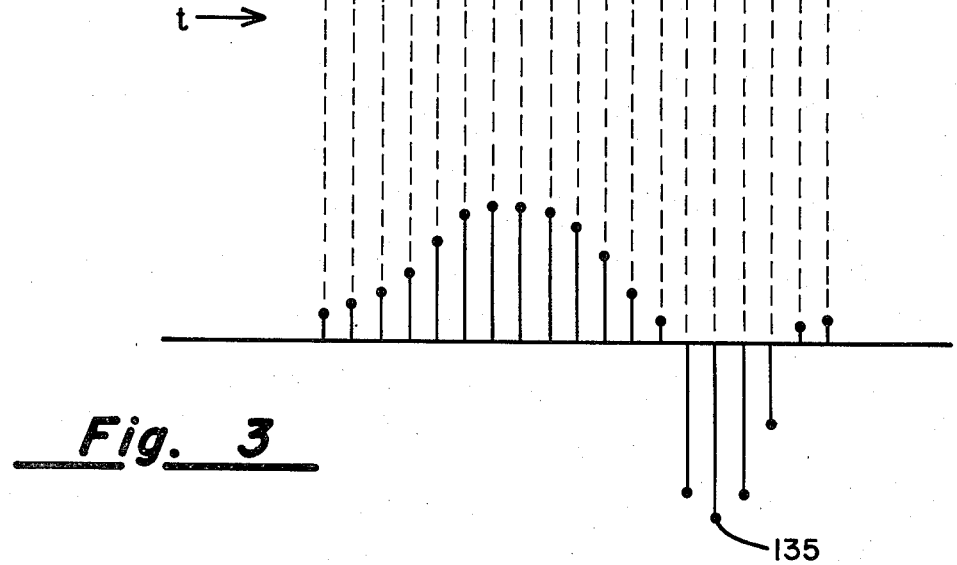
FIG. 3 shows a plot of the slopes of pertinent points of FIG. 2.

FIG. 2 shows a portion of a respiration waveform having discreet sampling intervals related thereto. Waveform points 20, 21, 22, . . . 39, each represent an instantaneous voltage magnitude obtained by voltage sampling the waveform at a regular sampling rate. Since the sampling rate is uniform, a representation of the slope of any line segment between any two points may be made by merely subtracting the magnitudes of the voltages at these points. In the preferred method, the slope is calculated between points spaced apart by at least one measurement interval, in order to minimize the effects of noise upon the sample points. For example, the voltage magnitude at 25 is subtracted from the voltage magnitude at 27, and this subtraction provides a measure of the slope of the line segment joining these two points. This slope may be represented as occurring at 26. Similarly, the voltage magnitude at 26 is subtracted from the voltage magnitude at 28, and this difference represents the slope at 27. FIG. 3 illustrates the slopes so represented at the various sample points of the waveform illustrated in FIG. 2. The maximum slope of this waveform is represented on FIG. 3 at 135. Note, that since the present method is concerned only with the magnitude of the slope the negative direction of the slope should be disregarded.

The preliminary method steps required for the practice of the method herein described involve the determination of a "threshold" slope value. This is accomplished by the steps illustrated in FIGS. 2 and 3, wherein the process is continued for a time period of four seconds. The maximum slope obtained during this four second time interval is determined and retained, and the cycle is repeated for thirty-one additional four second time intervals. After this time, thirty-two different maximum slope values have been retained, and the average of these thirty-two values is calculated to determine a "bench mark" slope value. The "bench mark" slope value is multiplied by 0.25 to set the "threshold" slope value. The "threshold" slope value is used as described hereinafter for constantly monitoring and detecting for the apnea condition.

However, a new "threshold" value is calculated approximately every two minutes so that major variations in patient respiration can be followed.

There are several exceptions to the step of periodically recalculating the "threshold" value. One of these is when an apnea event is detected during any four-second interval, in which case no maximum slope is calculated for that interval. A second exception occurs during any two minute interval wherein the average "bench mark" value exceeds the value calculated during the previous two minute interval by more than 1.5. In this case, it is assumed that a temporary abnormal respiration event has occurred, which event may be a sigh or moment of deep breathing, but which is not related to apnea or to so-called "normal" breathing patterns. In this event the "bench mark" is set at 1.5 times the "bench mark" previously calculated for the previous two minute interval, and is maintained at this calculated level until a new calculation is made.

Having determined a "threshold" value according to the steps hereinbefore described, this value is used to determine whether the likelihood of an apnea event is occurring. As the normal sampling continues during respiration, and the calculation of waveform slopes continues, each of the slopes so calculated is compared against the "threshold" value. If any slope so calculated is less than the threshold value for three consecutive seconds, a probable apnea condition may be occurring. If such slopes continue for a selectable time period after this three second interval an alarm is set to indicate an apnea event. The alarm may be either a visual or audible alarm, but in the case of an unattended patient it is advisable to have an audible alarm. The sound of an alarm should be sufficient to awake the patient, and once the patient awakens the apnea event will cease. Since interrupted breathing in infants is not usually considered to be apnea until the duration extends to about 20 seconds, the selectable time interval which is chosen for indicating an alarm condition is normally set in the 10-30 second range.

Figure 4B:
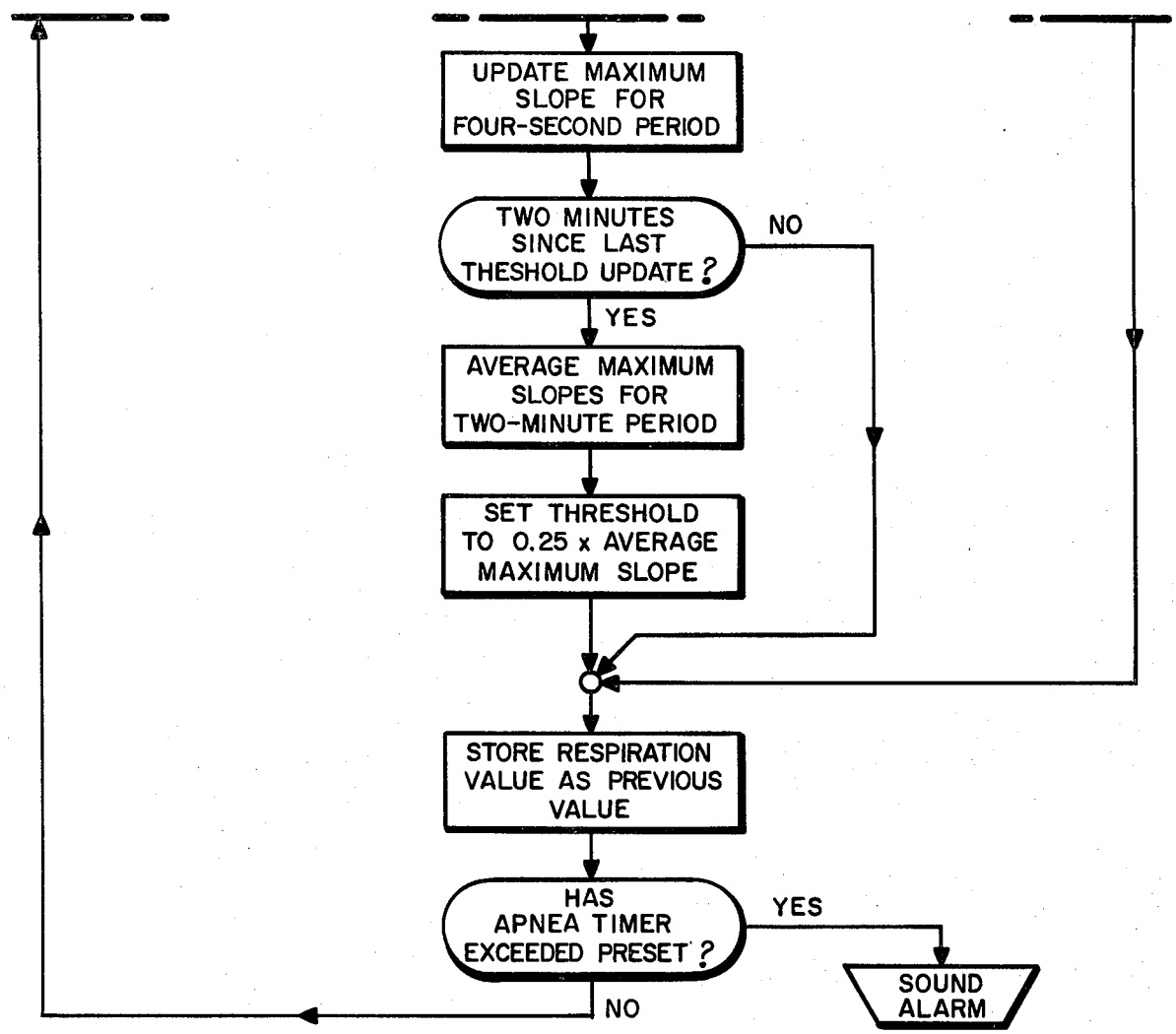

Referring next to FIG. 4, there is shown a flow chart of the method steps. The method is started by manual intervention of an operator and proceeds thereafter automatically until an apnea alarm condition is noted. It is presumed that the necessary and other electrical and other connections have been made to a patent monitoring device, and the method then proceeds through the performance of a number of steps of analysis and treatment of the electronic waveform produced by the monitor device, which waveform is representative of patient respiration. The waveform is sampled at uniform time intervals, which in the preferred embodiment is chosen to be eight samples per second. Each sample produces a value representative of the instantaneous waveform value at the time of the sample. Initially, two samples are required in order to enter into the overall method steps, each of the two samples being stored or retained as instantaneous respiration values. After two samples have been stored, the second previous value is subtracted from the current sample value, and this difference is converted to a number representative of an absolute value slope. During the first thirty-two times the method is performed, the maximum slope value is selected as a bench mark slope, and a threshold value is calculated by multiplying the bench mark by 0.25. Thereafter, this threshold value is updated approximately every two minutes by retaining the maximum slope values for four-second intervals over this two-minute period, and averaging the maximum slopes for the entire two-minute period.

After the method has been performed for a time period in excess of two minutes, there is retained a current threshold value which is utilized in a comparison with each subsequent slope value. If, in this comparison, the current slope value is greater than the current threshold value, normal respiration activity is presumed and the apnea timer is disabled. If the current slope value is less than the current threshold value, and if this condition has persisted for longer than two seconds, the apnea timer is set. The apnea timer therefore begins a timed runout, the duration of which is compared against a preset time, and when the timed runout equals the preset time the alarm is sounded and awakens the patient.

After the comparison of the current slope with the current threshold value the method proceeds through an updating sequence to adjust the threshold value if circumstances require. The maximum slope occurring over a four-second period is retained, and collected along with the maximum slopes occurring over thirty-two such four-second periods. These thirty-two maximum slope values are then averaged to derive an average maximum slope over approximately a two-minute period, and a threshold value is calculated by multiplying this value by 0.25. This threshold value is then utilized as a comparison base for further comparisons with current value slopes during the next subsequent two-minute time period.

The sequence shown in FIG. 4 is repeated eight times per second, the various loops illustrated on the flow chart being activated according to the conditions encountered during each repeat of the sequence. Special conditions described hereinbefore are not included on the flow chart, it being apparent when such special conditions are executed.

Figure 5:
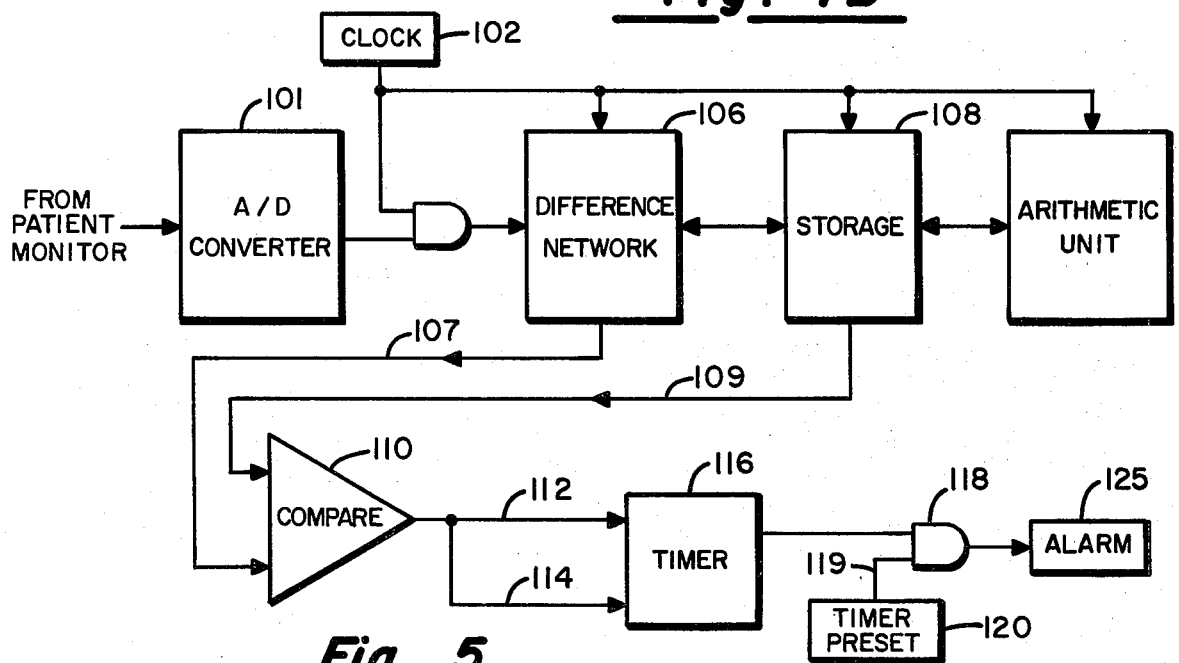
FIG. 5 shows a diagram of an apparatus for performing the method.

FIG. 5 shows a symbolic diagram of an apparatus for performing the method. An analog to digital converter (A/D) 101 is connected to receive the electrical signal from the patient monitor. A clock 102 produces timing pulses at the rate of eight pulses per second, and is coupled to gate 103. When a timing signal is applied to gate 103, the digital value representative of respiration waveform is gated into a difference network 106. Difference network 106 receives the second previous value from storage 108, and forms the difference between the current value and the second previous value. This difference value is transferred over line 107 to a comparison network 110, the other input being fed into comparison network 110 being a signal over 109 repesentative of current threshold value. The current threshold value is also retrieved from storage 108. In the event the current slope value is less than the current threshold value, line 112 into time 116 is activated, thereby starting timer 116. In the event the current slope is not less than the current threshold value line 114 into timer 116 is activated, thereby resetting timer 116 to zero. The output of timer 116 is fed into a gate 118, which gate also has as an input a signal over line 119 from timer preset 120. When timer 116 has run sufficiently long to equal or exceed the value set into timer preset 120, gate 118 becomes enabled and a signal is sent to activate alarm 125. Alarm 125 may be an audible alarm or visual alarm or combination thereof. Alarm 125 preferably includes an audible alarm, the loudness of which is preferably great enough to awaken the patient. It is known that an apnea condition which occurs during sleep may be terminated by merely awakening the patient, and alarm 125 serves this purpose.

In operation, the method is performed on a continuing and recurring basis after the preliminary setup steps are accomplished. First, the patient is connected to a monitoring device through suitable electrodes or transducers. Next, the patient is visably monitored to ascertain that a more or less steady state respiration condition exists. The patient monitoring apparatus is connected to the apparatus for performing the method, and the method is performed for at least a two minute period to permit the development of a first threshold value. Thereafer, the method is automatically performed at regular intervals until and unless an apnea condition is detected according to the teachings of the method. In this event, an audible and/or visual alarm is set and the method is terminated. Alternatively, the method may be continued even after detecting and indicating an alarm condition, by merely resetting the apnea timer and continuing the sequence described herein.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. A method of monitoring waveforms indicative of patient respiration and activating an alarm upon occurrence of predetermined respiration conditions indicative of apnea, comprising the steps of
   (a) monitoring a respiration waveform and forming a value representative of the instantaneous magnitude of said waveform at regular and continuous time intervals;
   (b) continuously forming the difference between each such value and at least the second previous such value, and developing therefrom a value representative of the instaneous slope of said waveform;
   (c) collecting such slope values for a first predetermined time which is at least as long in time as one respiration cycle and selecting from the collected slope values the maximum collected slope value;
   (d) continuously repeating step (c) for a second predetermined time which is longer than said first predetermined time, and forming the average of all maximum collected slope values;
   (e) forming a threshold value by selecting a predetermined fraction of said average of step (d);
   (f) comparing subsequent slope valves as found in step (b) with said threshold value of step (e) and activating said alarm when said subsequent slope values are less than the threshold value of step (e) for longer than a third predetermined time.

2. The method of claim 1, wherein said regular and continuous time intervals of step (a) are at least 8 times per second.

3. The method of claim 1, wherein the values developed in step (b) are converted to absolute magnitude values.

4. The method of claim 1, wherein said first predetermined time is at least four seconds.

5. The method of claim 1, wherein said second predetermined time is at least two minutes.

6. The method of claim 1, wherein said predetermined fraction is 1⁄4 .

7. The method of claim 1, wherein said third predetermined time is in the range of ten to thirty seconds.

8. The method of claim 2, wherein said first predetermined time is at least four seconds.

9. The method of claim 8, wherein said second predetermined time is at least two minutes.

10. The method of claim 9, wherein said predetermined fraction is ¼.

11. The method of claim 10, wherein said third predetermined time is in the range of ten to thirty seconds.

12. A method of monitoring patient respiration waveforms and activating an audible alarm upon occurrence of predetermined respiration conditions indication of apnea, comprising
   (a) sampling a respiration waveform at a predetermined sampling rate and recording instantaneous waveform magnitude values obtained from such sampling;
   (b) subtracting recorded instantaeous magnitude values from previously recorded instantaneous magnitude values and developing therefrom values representative of instantaneous rate of change of respiration;
   (c) selecting the maximum rate of change value occurring over a first predetermined time period which is at least as long as one respiration cycle;
   (d) continuously repeating step (c) for a second predetermined time period which is longer than said first time period and accumulating the selected maximum rate of change values over said first and second predetermined time periods;
   (e) averaging the accumulated maximum rate of change values and forming a threshold value by developing a value which is a predetermined fraction of said averaged values, said fraction being less than one;

(f) comparing said threshold value against subsequent values representative of instantaneous rate of change of respiration as developed in step (b); and (g) activating an alarm whenever said threshold value exceeds said values representative of instantaneous rate of change of respiration for a third predetermined time interval.

13. The method of claim 12, wherein said predetermined sampling rate is at least 8 samples per second.

14. The method of claim 12, wherein said step of subtracting further comprises subtracting a recorded instantaneous respiration value from a second previous recorded instantaneous respiration value.

15. The method of claim 12, wherein said first predetermined time interval is at least four seconds.

16. The method of claim 12, wherein said second predetermined time interval is at least two minutes.

17. The method of claim 12, wherein said predetermined fraction is substantially ¼.

18. The method of claim 12, wherein said third predetermined time interval is in the range of ten to thirty seconds.

19. The method of claim 13, wherein said step of subtracting further comprises subtracting a recorded instantaneous magnitude value from a second previous recorded instantaneous magnitude value.

20. The method of claim 14, wherein said first predetermined time interval is at least four seconds.

21. The method of claim 15, wherein said second predetermined time interval is at least two minutes.

22. The method of claim 16, wherein said predetermined fraction is substantially ¼.

23. The method of claim 17, wherein said third predetermined time interval is in the range of ten to thirty seconds.

* * * * *